US011045573B2

United States Patent
Tirén (10) Patent No.: US 11,045,573 B2
(45) Date of Patent: Jun. 29, 2021

(54) SYSTEM FOR TREATING A FLUID WITH NON-MERCURY-BASED UV LIGHT

(71) Applicant: Lightlab Sweden AB, Uppsala (SE)

(72) Inventor: Jonas Tirén, Uppsala (SE)

(73) Assignee: Lightlab Sweden AB, Uppsala (SE)

( * ) Notice: Subject to any disclaimer, the term of this patent is extended or adjusted under 35 U.S.C. 154(b) by 0 days.

(21) Appl. No.: 16/302,896

(22) PCT Filed: Jun. 20, 2017

(86) PCT No.: PCT/SE2017/050674
§ 371 (c)(1),
(2) Date: Nov. 19, 2018

(87) PCT Pub. No.: WO2017/222459
PCT Pub. Date: Dec. 28, 2017

(65) Prior Publication Data
US 2019/0298879 A1    Oct. 3, 2019

(30) Foreign Application Priority Data

Jun. 22, 2016   (SE) .................................... 1650889-7

(51) Int. Cl.
*A61L 9/20*         (2006.01)
*A61L 2/10*         (2006.01)
(Continued)

(52) U.S. Cl.
CPC .................... *A61L 9/20* (2013.01); *A61L 2/10* (2013.01); *A61L 2/26* (2013.01); *C02F 1/325* (2013.01);
(Continued)

(58) Field of Classification Search
USPC ........................................................ 250/436
See application file for complete search history.

(56) References Cited

U.S. PATENT DOCUMENTS

| 4,336,223 A * | 6/1982 | Hillman ................... A61L 2/10 |
| | | 210/103 |
| 6,389,970 B1 | 5/2002 | Tashiro et al. |

(Continued)

FOREIGN PATENT DOCUMENTS

| DE | 102010005893 A1 | 7/2011 |
| EP | 1874895 A2 | 1/2008 |

(Continued)

OTHER PUBLICATIONS

Gawande, A.B. et al., "Luminescence improvement in Pr3+ and Gd3+ activated Sr2MG(BO3)2 inorganic phosphor," Materials Research Bulletin 60: 285-291, 2014.

(Continued)

*Primary Examiner* — Phillip A Johnston
(74) *Attorney, Agent, or Firm* — RMCK Law Group, PLC (57) ABSTRACT

The present invention generally relates to a system for treating a fluid and specifically to a treatment system configured for improved bacterial reduction, wherein the system comprises a field emission based UV light source adapted to emit light within a ultraviolet C (UVC) spectrum with a wavelength range having an upper range limit being higher compared to light emitted from a mercury based UV light source.

18 Claims, 7 Drawing Sheets

(51) Int. Cl.
| | |
|---|---|
| *A61L 2/26* | (2006.01) |
| *C02F 1/32* | (2006.01) |
| *C09K 11/77* | (2006.01) |
| *H01J 61/20* | (2006.01) |
| *H01J 61/44* | (2006.01) |

(52) U.S. Cl.
CPC ........ *C09K 11/778* (2013.01); *C09K 11/7709* (2013.01); *C09K 11/7774* (2013.01); *C09K 11/7777* (2013.01); *H01J 61/20* (2013.01); *H01J 61/44* (2013.01); *A61L 2202/11* (2013.01); *A61L 2202/122* (2013.01); *A61L 2202/14* (2013.01); *A61L 2209/111* (2013.01); *A61L 2209/12* (2013.01); *C02F 2201/326* (2013.01); *C02F 2201/328* (2013.01); *C02F 2201/3222* (2013.01); *C02F 2201/3223* (2013.01); *C02F 2201/3227* (2013.01); *C02F 2209/40* (2013.01); *C02F 2303/04* (2013.01)

(56) References Cited

U.S. PATENT DOCUMENTS

| | | | |
|---|---|---|---|
| 6,447,721 B1 | 9/2002 | Horton, III et al. | |
| 7,336,023 B2* | 2/2008 | Youh | C09K 11/54 313/112 |
| 8,506,886 B2* | 8/2013 | Owen | H05B 3/0052 422/24 |
| 8,841,146 B2* | 9/2014 | Yen | H01L 33/0095 257/E21.528 |
| 8,946,993 B2* | 2/2015 | Murnick | H01J 63/02 313/486 |
| 9,168,320 B1 | 10/2015 | Wedding et al. | |
| 9,288,885 B2 | 3/2016 | Hu | |
| 9,617,171 B2* | 4/2017 | Rajagopalan | C02F 1/325 |
| 9,987,499 B2* | 6/2018 | Hayashi | A61N 5/0616 |
| 2005/0010249 A1 | 1/2005 | Minamoto et al. | |
| 2007/0248487 A1* | 10/2007 | Kay | C02F 1/325 422/24 |
| 2012/0168679 A1 | 7/2012 | Huang et al. | |
| 2014/0131619 A1 | 5/2014 | Greuel et al. | |

FOREIGN PATENT DOCUMENTS

| | | |
|---|---|---|
| JP | 2011055898 A | 3/2011 |
| WO | 9857344 A1 | 12/1998 |
| WO | 2006109238 A2 | 10/2006 |
| WO | 2008156813 A1 | 12/2008 |
| WO | 2009139908 A1 | 11/2009 |
| WO | 2017003347 A1 | 1/2017 |

OTHER PUBLICATIONS

International Search Report and Written Opinion dated Sep. 22, 2017 for PCT Application No. PCT/SE2017/050674, 13 pages.

Swedish Search Report dated Feb. 28, 2017 for Swedish Patent Application No. 1650889-7, 2 pages.

Jüstel, T. et al., Temperature-dependent spectra of YPO4:Me (Me = Ce, Pr, Nd, Bi), Journal of Luminescence, vol. 106, 2004, pp. 225-233.

Kim, S. et al., "Using UVC Light-Emitting Diodes at Wavelengths of 266 to 279 Nanometers to Inactivate Foodborne Pathogens and Pasteurize Sliced Cheese," Applied and Environmental Microbiology, vol. 82, No. 1, Jan. 2016, pp. 11-17.

PCT International Search Report and Written Opinion dated Jan. 23, 2018 for International Application No. PCT/SE2017/051183, 11 pages.

Extended European Search Report dated Jan. 17, 2020 for EP Application No. 17815816.8, 10 pages.

* cited by examiner

SYSTEM FOR TREATING A FLUID WITH NON-MERCURY-BASED UV LIGHT

CROSS-REFERENCE TO RELATED APPLICATIONS

This application is a 371 U.S. National Stage of International Application No. PCT/SE2017/050674, filed Jun. 20, 2017, which claims priority to Swedish Application No. 1650889-7, filed on Jun. 22, 2016. The disclosures of each of the above applications are incorporated herein by reference in their entirety.

TECHNICAL FIELD

The present invention generally relates to a system for treating a fluid and specifically to a treatment system configured for improved bacterial reduction, wherein the system comprises a field emission based UV light source adapted to emit light within a ultraviolet C (UVC) spectrum with a wavelength range having an upper range limit being higher compared to light emitted from a mercury based UV light source.

BACKGROUND OF THE INVENTION

Systems for disinfection of water, air, surfaces or certain equipment using ultraviolet (UV) light generated by low pressure mercury lamps (LP-Hg lamps), predominantly emitting wavelengths around 254 nm, are commonly used today. Medium and/or high-pressure Hg lamps may alternatively be used, for example in large systems such as for water disinfection as these lamps may deliver higher power output. These systems may be combined with particle filtering, reverse osmosis (for water disinfection) and other. The systems are popular since they do not use any chemicals (e.g. chlorine), which is advantageous for many reason, environmental not the least.

These light sources work well, can have a good energy efficiency (for larger low pressure Hg lamps this may in the range of 30-35%) and have lifetimes that for the best products today, are well above 10 000 hours; 16 000 hours is reported for the best products. Other UV sources (e.g. Excimer light sources) exist but have reportedly either a very short life time (<500 hours) or a very low energy efficiency (e.g. UVC-LED typically in the order of 1%).

A serious drawback with LP-Hg light sources is that the light source de-activates (kills) bacteria to a certain level, after which no significant reduction is seen. This phenomenon is generally referred to as "tailing". There are several (somewhat different) explanations found in the literature for this; the most accepted is that the bacteria will have a process of self-repair. If the rate of such a process is the same as the de-activation process the net result would be a steady state condition. Typically, in tests performed, Hg-lamps do not reach below $10^2$-$10^3$ Colony Forming Units per milliliter (CFU/ml) for a generally used microorganism for this kind of testing and validation, i.e. *Escherichia coli* bacteria (*E. coli*).

Now, after the disinfection the micro-organisms will start to multiply again, after a so called lag period, i.e. an initial period under which no growth is observed. For *E. coli* the doubling rate, a.k.a. the generation rate, i.e. the time it takes for the bacteria to double their numbers, may typically be considered to be in the order of 20 minutes. This rate is depending on many other parameters such as pH, access to nutrient etc. In water that has been disinfected, the nutrients may for example be the de-activated microorganisms. An unwanted consequence of this is that the disinfected water typically will become re-infected after some period of time.

With the above in mind, there is thus a desire to provide further enhancements to an UV disinfection system for treating a fluid, specifically addressing the tailing effect as mentioned above.

SUMMARY OF THE INVENTION

According to an aspect of the invention, the above is at least partly alleviated by a system for treating a fluid, comprising a container arranged to receive an amount of a fluid, a first UV light source contained within the container, and an electrical power supply operatively associated with the first UV light source, the electrical power supply arranged to provide electrical power to the first UV light source for treating the amount of the fluid received within the chamber using the first UV light source, wherein the first UV light source is a non-mercury based UV light source adapted to emit light within the ultraviolet C (UVC) spectrum with a wavelength range having an upper range limit being higher compared to light emitted from a mercury based UV light source.

The inventor of the present invention has surprisingly identified that the tailing effect may be reduced in case of introduction of an UV light source emitting lighting within a wavelength range being at least slightly higher as compared to what is possible to achieve using a mercury based UV light source. For example the above mentioned LP-Hg lamps typically emit radiation that is predominately narrow peak around 254 nm. The use of an UV light source at least partly emitting radiation in preferably a broader and more continuous spectrum being at least partly above 254 nm will according to the invention thus provide for an improved disinfection effect as compared to the normal prior-art case where a narrow (wavelength) banded mercury based UV light source is used.

In a preferred embodiment, the first light source is configured to emit radiation within a wavelength range from around 240 nm to at least 270 nm, thereby at least partly overlapping the normal emission provided by mercury based UV light sources. In a possible embodiment the wavelength range for light emitted from the first UV light source is from around 240 nm to around 400 nm. It is preferred to allow the first UV light source to emit light having a wavelength interval including emission of UV radiation at 265 nm, being a possible peak value for germicidal effectiveness.

Furthermore, the invention advantageously allows for the possibility of reducing the amount of remaining bacteria in the fluid to below 100-1000 colony forming units (CFU) per milliliter (mL), as the treatment system does not solely rely on the use of a mercury based light source.

In a preferred embodiment of the invention, the first UV light source comprises at least one of a field emission light source (FEL). Alternatively, the first UV light source may comprise e.g. a plurality of UVC-LEDs and/or a combination of light sources based on different technologies to suit the application. The UVC-LEDs may additionally have several different wavelength peaks in order to better cover a specific wavelength range.

Furthermore, emerging technologies such as field emission light sources (FEL) and UVC Light Emitting Diodes (LEDs) offers turn on times that are in the order of milliseconds, mainly governed by the electronic drive unit. In comparison, Hg-LP lamps typically need a warm up time in the range of a few minutes before they will reach full output power. UVC-LEDs are currently being developed but are at this time exhibiting reportedly short life times and very low energy efficiencies. Significant efforts are being used in order to improve this and may surely and eventually be successful. Field emission light sources on the other hand may have life times in the order of 1000-6000 hours depending on the desired power density and have been measured to reach efficiencies around 10%, albeit 4-5% in the UVC region.

An advantageous effect with using a field emission light source as the first UV light source is that such a light source may be configured to emit UV light at a spectrum that is not a distinct peak around 254 nm but a more continuous spectrum in above mentioned range of 240-320 nm. Field emission UVC lamps have demonstrated the capability to continue the disinfection process and do not exhibit any significant tailing effect.

To build a water disinfection system that both have excellent germicidal properties as well as a system that has good energy efficiency and long life time it would be beneficial to combine the two technologies, i.e. using a mercury based lamp to de-activate the microorganisms by 4 orders of magnitude and use a Field Emission UVC source to reduce the microorganisms by yet another 2-4 orders of magnitude. The further reduction may be decided on considerations concerning what is more important of for example energy efficiency, system life time and germicidal effectiveness. Such systems may be implemented in several ways as will be described below.

In a preferred embodiment of the invention the system further comprising a second UV light source operatively associated with the power supply, wherein the second UV light is a mercury based UV light source. The second UV light source (i.e. the mercury based UV light source) typically has a longer life time and higher energy efficiency than the first light source. However, by combining the effect of the long life and high efficiency second UV light source with the positive germicidal effect provided by the first UV light source, an overall improvement of the treatment system may be achieved, having an improved germicidal effectiveness as compared to a normal prior-art system solely comprising a mercury based UV light source.

In a possible embodiment of the invention, the electrical power supply is configured to selectively activate the first UV light source based on a predetermined condition. It could for example be possible to e.g. periodically sample the treated bacteria level within the fluid, to determine to what extent the first UV light source needs to be involved in the disinfection process.

In another embodiment of the invention it may also be possible to equip the system with a sensor for measuring an UV intensity level within the container, where the sensor for measuring the UV intensity level is arranged in communication with a control unit comprised with the treatment system. The control unit may be arranged to selectively activate the first and the second UV light source depending on the UV intensity level, for example within different wavelength intervals and possibly dependent of different requirements for treatment of the fluid.

Preferably, at least one of the first and the second UV light source at least partially extends into the amount of the fluid received within the container. The container may for example be divided into a first and a second portion, the first portion holding the first UV light source and the second portion holding the second UV light source. Thereby, the fluid may be arranged to first receive light from one of the UV light sources, and then from the other one of the UV light sources. In one embodiment of the invention the fluid is firstly receiving UV light radiated from the second UV light source.

Further features of, and advantages with, the present invention will become apparent when studying the appended claims and the following description. The skilled addressee realize that different features of the present invention may be combined to create embodiments other than those described in the following, without departing from the scope of the present invention.

BRIEF DESCRIPTION OF THE DRAWINGS

The various aspects of the invention, including its particular features and advantages, will be readily understood from the following detailed description and the accompanying drawings, in which.

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled addressee. Like reference characters refer to like elements throughout.

Other applications such as air disinfection, surface disinfection, etc., are equally possible and the system implementations described are generally equally valid. It is also obvious to the skilled person that scaling and different combinations of the described implementations are straightforward. As an example, the figures are showing light sources of similar size and shape for practical reasons, but they may in fact have completely different sizes as well as different form factors (shapes). Furthermore, there may be additional light sources in such systems.

Figure 1:
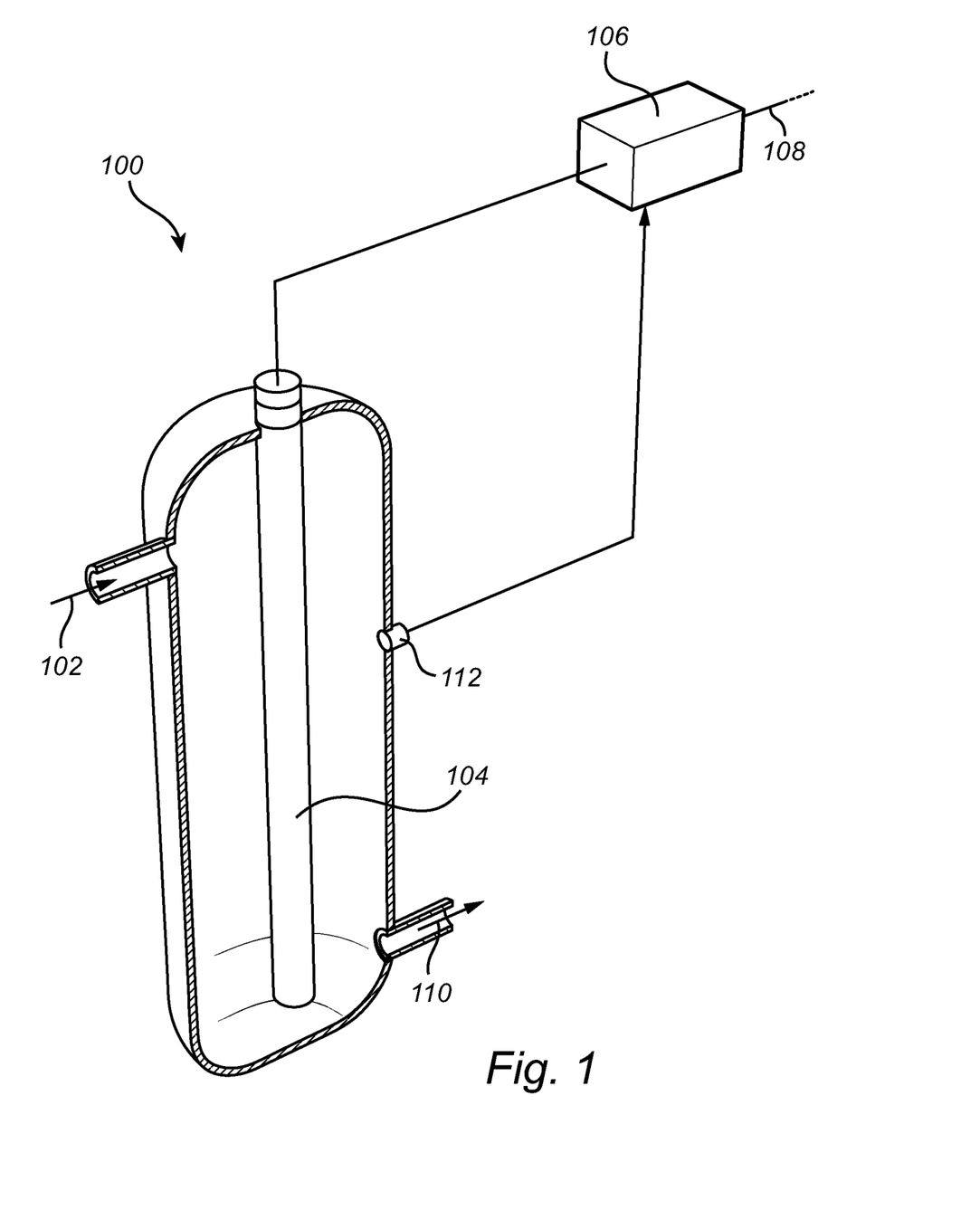
FIG. 1 shows an example of a prior-art fluid treatment system.

Referring now to the drawings and to FIG. 1 in particular, there is illustrated a typical simple fluidic UV disinfection system 100 of the current state of the art is shown in cross sectional view. It should be noted that the complete system usually may contain filters of different kinds as well as other components. Here only the UV disinfection section is described.

A fluid, such as water, enters the disinfection tube through the inlet 102 into a container arranged to receive an amount of the fluid. A light source 104, most commonly being a low pressure mercury (Hg) based UV light source, is turned on and energized by an electronic drive unit (ballast) 106. The light source 104 is commonly additionally protected by a UV transmitting sleeve (not shown, applicable to all embodiments) to prevent Hg to enter the water should the Hg light source break. The disinfection tube may in some embodiment comprise various structures or means to provide a turbulent flow in order to further ensure that all organisms are being subjected to an as large amount of UV radiation as possible, such structures and means also not shown. The electronic drive unit 106 is in turn connected to a power supply 108, such as a wall electrical outlet or similar. The electronic power supply may further be integrated with the disinfection tube or the light source. The water flows by the light source 104 and exits through an outlet 110. The UV intensity may be monitored by an UV sensor 112, connected to the electronic drive unit 106 which is safeguarding the system for adequate UV intensity to ensure adequate disinfection. The intensity may change for example due to different transmittance of the fluid and/or due to intensity variation of the light source. The electronic drive unit 106 may further control a variable valve (not shown), thus controlling the flow rate by using the UV intensity to determine a maximum value of the flow and thereby ensuring disinfection performance. Further sensors may comprise temperature and pressure (not shown here).

Figure 2:
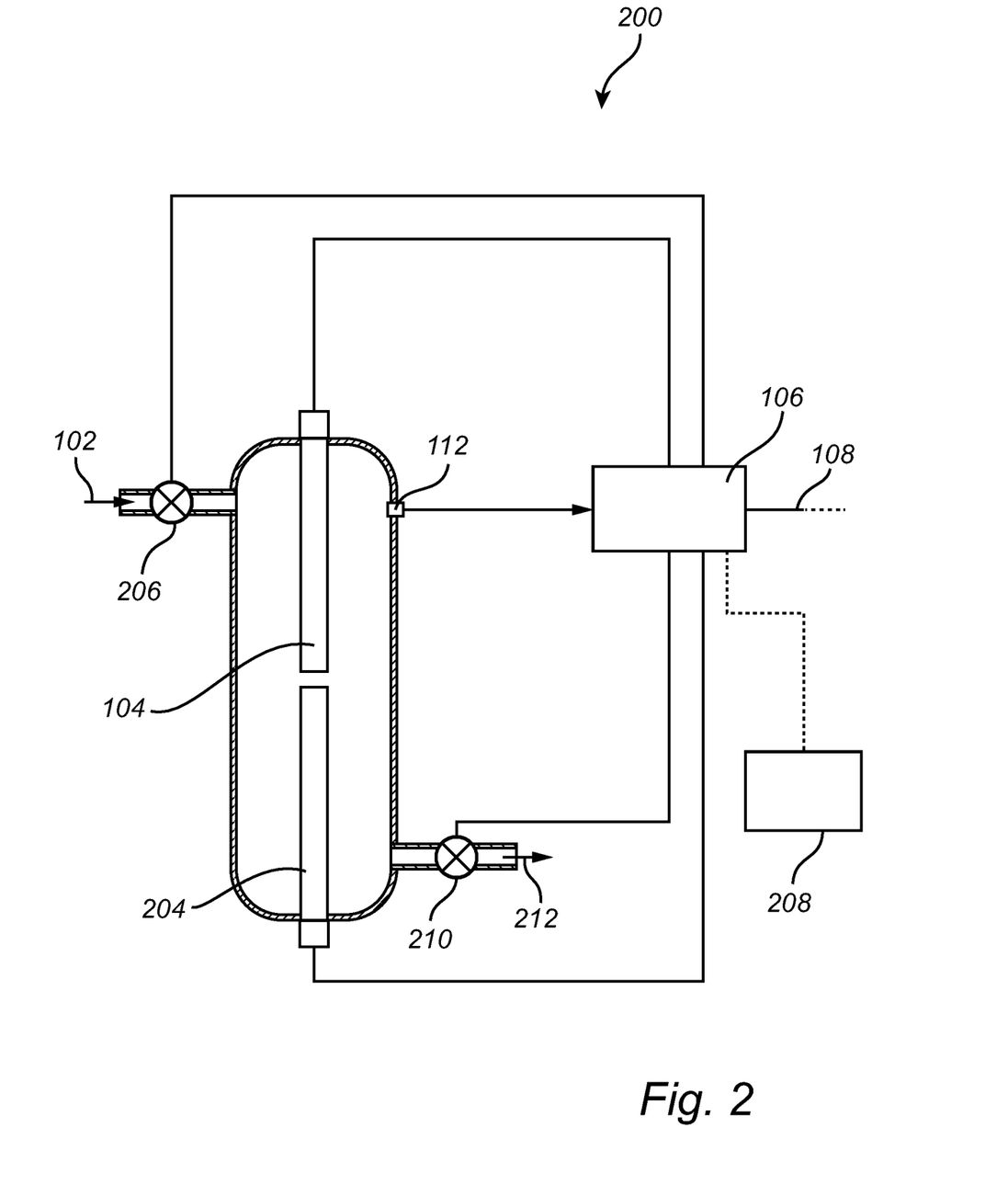
FIG. 2 provides an exemplary embodiment of the inventive system for treating a fluid.

A first preferred embodiment of the present invention is conceptualized in FIG. 2 and the discussion below. In this case, the two light sources 104 and 204 are integrated into a single disinfection tube/arrangement 200. Specifically, water enters the water treatment arrangement 200 through an inlet 102 here controlled by (an optional) inlet valve 206. The electronic drive unit 106, which may be using a remote control device 208 (wire bound or wireless) will turn on both the Hg light source 104 and additional UV light source 204 that exhibits no significant tailing effect as soon as the input valve 206 is open, the additional light source 204 being a non-mercury based UV light source. The electronic drive unit 106 will also open an output valve 210, ensuring that the fluid flows by both light sources 104, 204, now leaving the disinfection tube through an outlet 212. It may be advantageous to ensure short delays between for example opening the output and input valve. Again, a UV-sensor 112 may be used to monitor the UV intensity at the inner wall of the water treatment arrangement 200.

Figure 3:
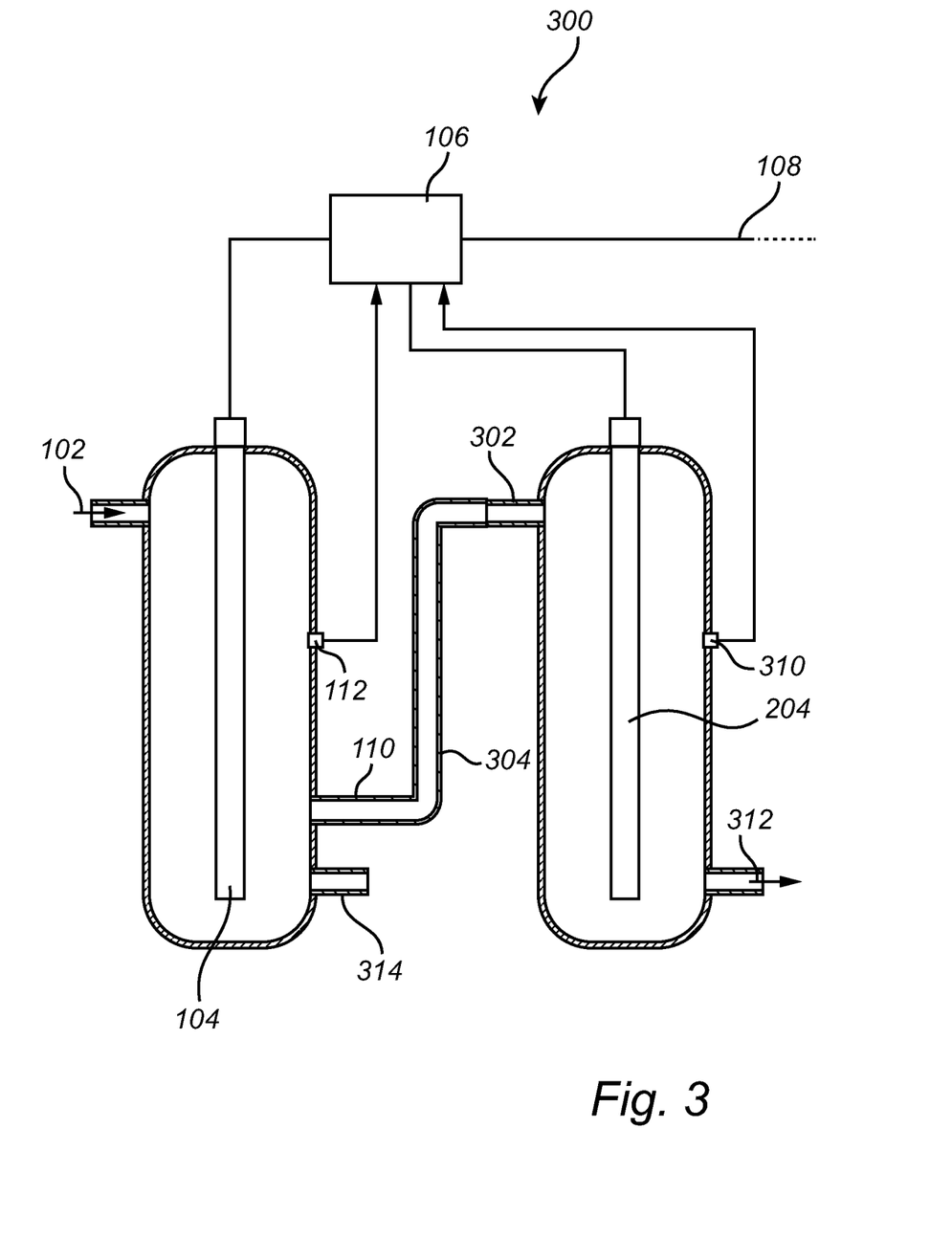
FIG. 3 illustrates an alternative embodiment of the inventive system for treating a fluid.

Now turning to FIG. 3, showing a second preferred embodiment of a treatment system 300. This embodiment consists of two similar systems connected in series, one with the Hg light source and the other with a light source that exhibits no significant tailing effect. The order of the two can be different as compared to what is shown in FIG. 3. It should be noted that the first stage in the water disinfection is similar to what is outlined in FIG. 2 above and thus not further discussed. Water to be processed enters inlet 102, passes by the Hg light source 104, and leaves the first container through outlet 110. A conduit 304 connects the outlet 110 to an inlet 302 of a second container comprising the non-Hg light source 204. The processed water passes the second light source 204 and exits the second container through an outlet 312.

Additionally, in the embodiment shown in FIG. 3 the first container comprising the first light source 104 is provided with a second outlet 314, i.e. where the water is only passing by the first light source 104, for example suitable for situations where the water may be used also when it has not reached the highest level of disinfection. In comparison, the water exiting the outlet 312 will have passed by both the first 104 and the second 204 light source, having undergone both UVC treatments and thus is highly disinfected and may for example be more suited as drinking water.

The Hg light source 104 and the additional UV light source 204 that exhibits no significant tailing effect are powered by the electronics drive unit 106, which may or may not be integrated to contain drive units for both light sources (as shown) or be separated (not shown). The electronic drive unit 106 may further be partitioned in several ways, including partially or fully being integrated with e.g. the light sources 104, 204. Other possibilities for partitioning the electronic drive unit 106 are numerous and within the scope of the invention. The intensity of the additional UV light source 204 may be monitored by an additional UV sensor 310. The intensity is fed-back to the electronic drive 106 unit which may comprise the functionality for controlling the intensity of the additional UV light source 204. In all embodiments it should be noted that it is further possible to allow the user to decide if the water should be further disinfected or not, this way saving overall power consumption and lamp life. This implementation may easily be done by introducing e.g. a switch (not shown). Preferably indications of which state the system is in e.g. Light Emitting Diodes of different colors, a display, or other means may be used.

Figure 4A:
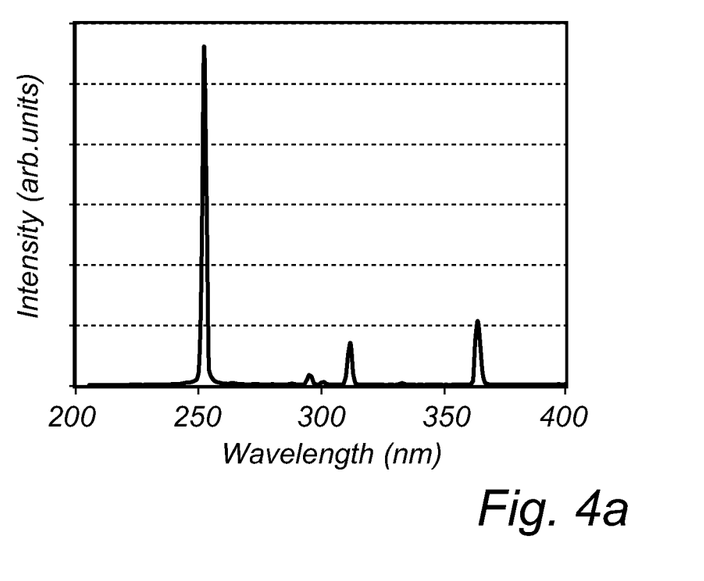
FIGS. 4a-b illustrates the emission spectra from an Hg light source and its corresponding germicidal de-activation curve.

Turning now to FIGS. 4a and b, 5a-f. Note that all measured de-activation curves show the relative reduction as function of UV dose in order to be comparable, thus the vertical axis shows the logarithm of the ratio between the remaining concentration of E. coli in Colony Forming Units per milliliter (CFU/ml)–denoted N–the initial concentration before irradiation, denoted $N_o$, thus denoted log(N/No).

Figure 4B:
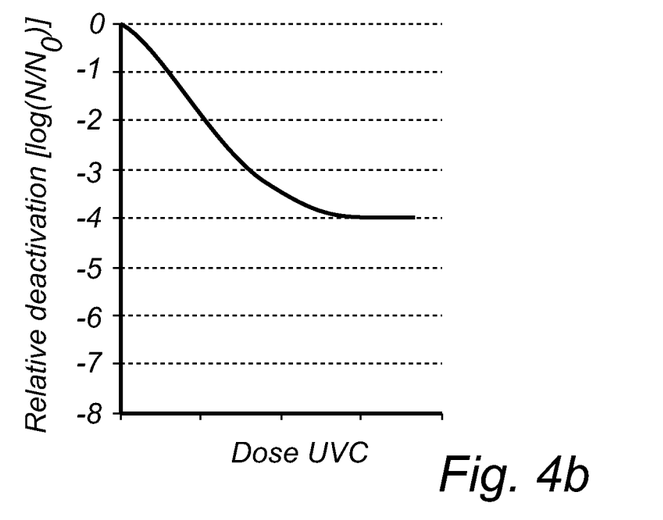

As can be seen in FIG. 4a, a LP-Hg lamp essentially emits a strong relatively sharp peak at around 254 nm. FIG. 4b shows the corresponding deactivation of *Escherichia coli* (*E. coli*) in tap water. As can be seen, a certain level of *E. coli* is reached after which no further reduction is seen, i.e. the curve flattens over time at a set level.

Figure 5A:
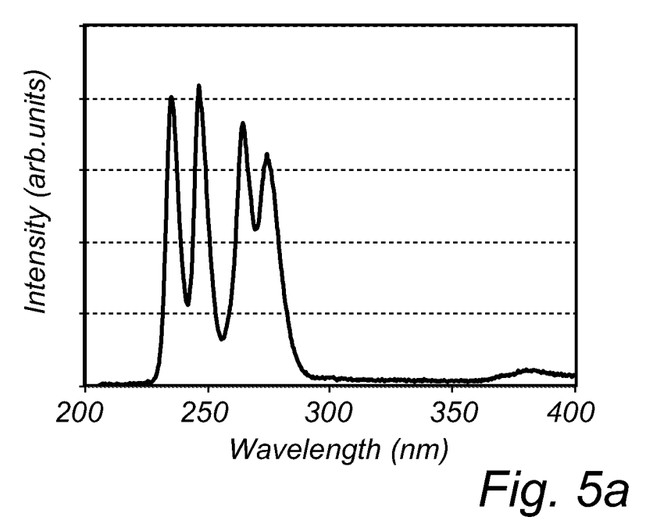
FIGS. 5a-f illustrate different emission spectra resulting from different phosphor material and their corresponding germicidal de-activation curves.

In FIGS. 5a-4f, the beneficial de-activation of *E. coli* of the inventive system is illustrated.

Figure 5B:
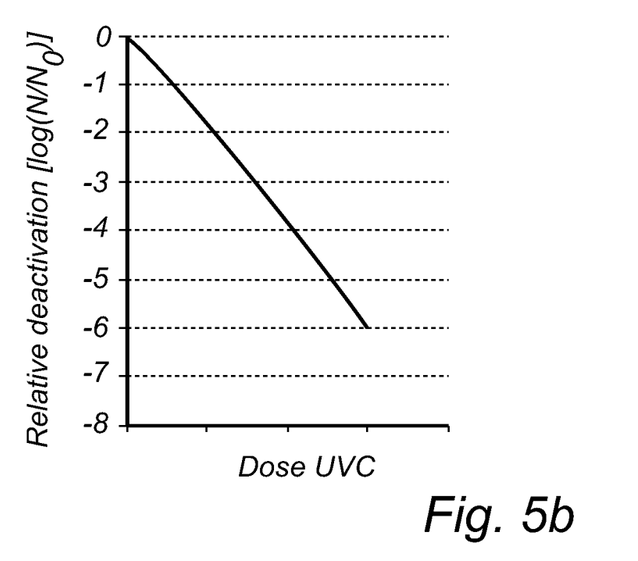

In FIG. 5a, the emission spectra from an UVC field emission light source provided with a first phosphor material (light powder) for UV light emission is provided. In FIG. 5a, the phosphor material has been selected to be a $LuPO_3:Pr^{3+}$ phosphor material (or equivalent). In FIG. 5b, the corresponding de-activation curve is shown, for disinfection of water, where no significant tailing is visible.

Figure 5C:
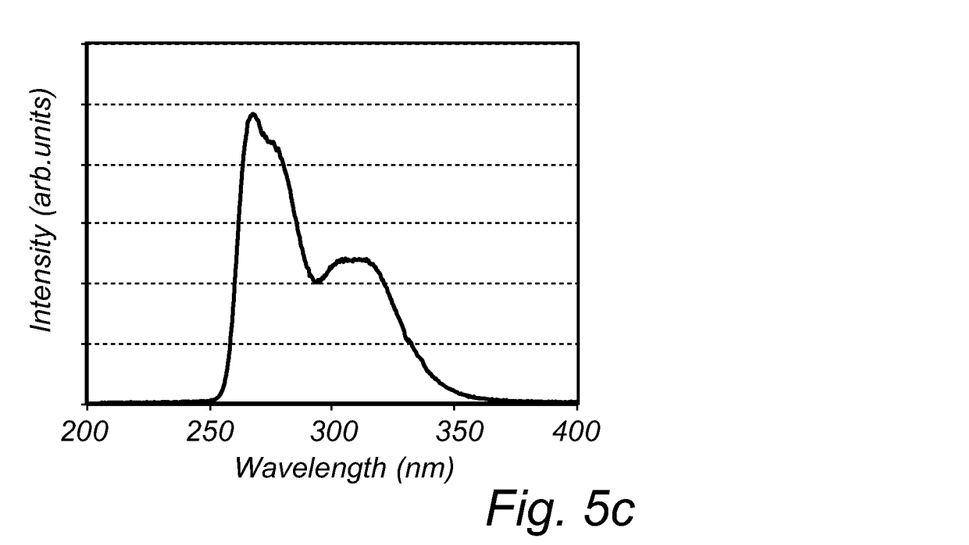
Figure 5D:
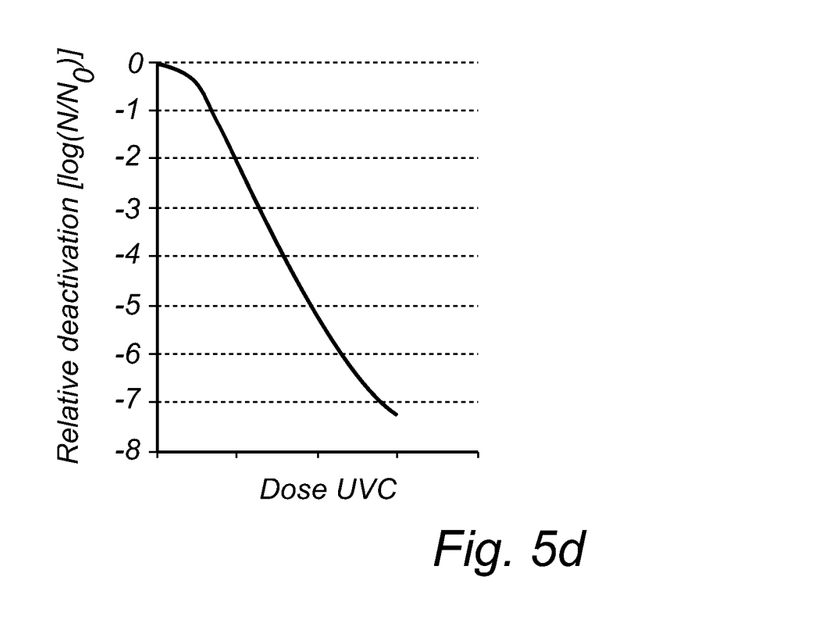

In FIG. 5c, a second phosphor material in the form of a $Lu_2Si_2O_7:Pr^{3+}$ phosphor material is used, and FIG. 5d shows the corresponding de-activation curve. As may be seen, in FIG. 5d, a de-activation of almost 8 orders of magnitude has been achieved, i.e. 99.999999% of the bacteria have been de-activated.

Figure 5E:
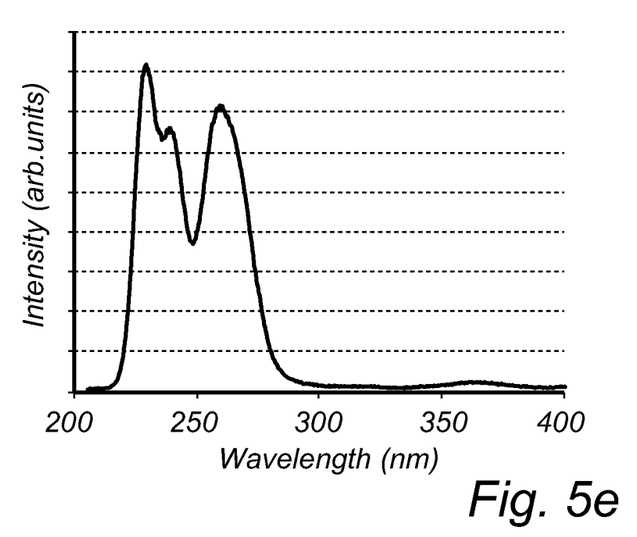
Figure 5F:
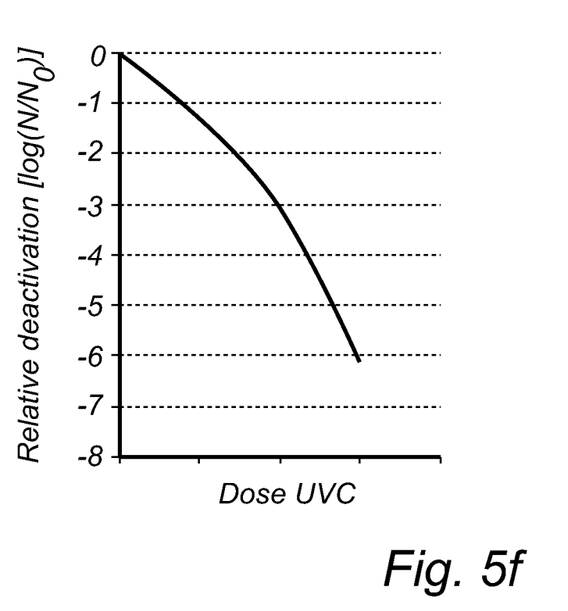

Turning finally to FIGS. 5e and 5f, where a third phosphor material in the form of a $LaPO_4:Pr^{3+}$ phosphor material is used and the corresponding de-activation curve is shown, respectively.

Furthermore, additional phosphor materials such as $YBO_3:Pr^{3+}$ and $YPO_4:Bi^{3+}$ have been evaluated with similar results.

In summary, the present invention relates to a system for treating a fluid, comprising a container arranged to receive an amount of a fluid, a first UV light source contained within the container, and an electrical power supply operatively associated with the first UV light source, the electrical power supply arranged to provide electrical power to the first UV light source for treating the amount of the fluid received within the chamber using the first UV light source, wherein the first UV light source is a non-mercury based UV light source adapted to emit light within the ultraviolet C (UVC) spectrum with a wavelength range having an upper range limit being higher compared to light emitted from a mercury based UV light source.

By means of the invention it is possible to further improve e.g. disinfection of the fluid by including an UV light source having a broader spectrum as compare to a prior-art treatment system where the UV radiation is solely provided to be predominately at around 254 nm. Specifically, as would be obvious from the illustrations provided in FIGS. 5a-5f, the benefits of using a non-mercury based UV light source for disinfection of bacteria comprised with e.g. water is apparent. The broader spectrum achieved with an UVC field emission light source provided with e.g. a $LaPO_4:Pr^{3+}$, $LuPO_3:Pr^{3+}$, $Lu_2Si_2O_7:Pr^{3+}$, $YBO_3:Pr^{3+}$ or $YPO_4:Bi^{3+}$ phosphor material (light powder) allows for a further bacterial reduction/deactivation, allowing for the possibility of providing a safer environment where clean water may be hard to acquire. It is equally possible to use multiple UVC-LED's with slightly different peak wavelength to achieve a similar effect.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps. Additionally, even though the invention has been described with reference to specific exemplifying embodiments thereof, many different alterations, modifications and the like will become apparent for those skilled in the art.

Variations to the disclosed embodiments can be understood and effected by the skilled addressee in practicing the claimed invention, from a study of the drawings, the disclosure, and the appended claims. Furthermore, in the claims, the word "comprising" does not exclude other elements or steps, and the indefinite article "a" or "an" does not exclude a plurality.

The invention claimed is:

1. A system for treating a fluid, comprising:
a container arranged to receive an amount of a fluid;
at least two different UV light sources contained within the container, the at least two different UV light sources comprising a first UV light source and a second UV light source different from the first UV light source, the first UV light source being a non-mercury field emission based UV light source and the second UV light source being a mercury based UV light source; and
an electrical power supply operatively associated with the at least two different UV light sources, the electrical power supply arranged to provide electrical power to the first and second UV light sources for treating the amount of the fluid received within the chamber using the first and second UV light sources,
wherein the first UV light source is adapted to emit both (i) light within the ultraviolet C (UVC) spectrum with a wavelength range having an upper range limit being higher compared to light emitted from the mercury based second UV light source, and (ii) radiation within a wavelength range between 320 nm and 400 nm,
wherein the second UV light source is configured to emit radiation at around 254 nm,
wherein the field emission based UV light source comprises a light converting material arranged to receive electrons and to emit UV light, and
wherein the light converting material is selected to be at least one of $LaPO_4:Pr^{3+}$, $LuPO_3:Pr^{3+}$, $Lu_2Si_2O_7:Pr^{3+}$, $YBO_3:Pr^{3+}$, or $YPO_4:Bi^{3+}$ in order to improve a deactivation curve for a selected microorganism.

2. The system according to claim 1, wherein the first UV light source is configured to emit radiation within a wavelength range between 240 nm and 320 nm.

3. The system according to claim 1, wherein the light converting material is a phosphor material.

4. The system according to claim 1, wherein the first UV light source further comprises at least one UVC Light Emitting Diode (LED).

5. The system according to claim 1, wherein the second UV light source comprises a Low-Pressure HG-lamp.

6. The system according to claim 1, wherein the electrical power supply is configured to selectively activate the first UV light source based on a predetermined condition.

7. The system according to claim 1, wherein the first and the second UV light source are activated essentially simultaneously.

8. The system according to claim 6, wherein the predetermined condition is a predetermined disinfection requirement for the fluid treated by the system.

9. The system according to claim 1, further comprising a sensor for measuring a UV intensity level within the container.

10. The system according to claim 1, wherein at least one of the first and the second UV light source at least partially extends into the amount of the fluid received within the container.

11. The system according to claim 1, wherein the container is divided in a first and a second portion, the first portion holding the first UV light source and the second portion holding the second UV light source.

12. The system according to claim 8, further comprising a control unit in communication with the sensor and configured for controlling the selective activation of the first and the second UV light source.

13. The system according to claim 1, wherein the first UV light source is configured to emit radiation at around 265 nm.

14. The system according to claim 1, wherein the electrical power supply is configured to selectively activate the first and second UV light sources based on a predetermined condition, wherein the predetermined condition is a sampled bacteria level of the fluid.

15. The system according to claim 1, further comprising a sensor for measuring a UV intensity level within the container, wherein the electrical power supply is configured to selectively activate the first and second UV light sources based on a predetermined condition, wherein the predetermined condition is the UV intensity level measured by the sensor.

16. The system according to claim 6, wherein the predetermined condition is a sampled bacteria level of the fluid.

17. The system according to claim 6, further comprising a sensor for measuring a UV intensity level within the container, wherein the predetermined condition is the UV intensity level measured by the sensor.

18. A system for treating a fluid, comprising:
a container arranged to receive an amount of a fluid;
at least two different UV light sources contained within the container, the at least two different UV light sources comprising a first UV light source and a second UV light source different from the first UV light source, the first UV light source being a non-mercury field emission based UV light source and the second UV light source being a mercury based UV light source; and an electrical power supply operatively associated with the at least two different UV light sources, the electrical power supply arranged to provide electrical power to the first and second UV light sources for treating the amount of the fluid received within the chamber using the first and second UV light sources, wherein the first UV light source is adapted to emit both (i) light within the ultraviolet C (UVC) spectrum with a wavelength range having an upper range limit being higher compared to light emitted from the mercury based second UV light source, and (ii) radiation within a wavelength range between 320 nm and 400 nm, wherein the second UV light source is configured to emit radiation at around 254 nm, wherein the non-mercury field emission based UV light source comprises a light converting material arranged to receive electrons and to emit UV light, the light converting material being selected to improve a deactivation curve for a selected microorganism, and wherein the electrical power supply is configured to selectively activate the first and second UV light sources based on a predetermined condition, wherein the predetermined condition is a sampled bacteria level of the fluid.

* * * * *